(12) United States Patent
Mangino

(10) Patent No.: US 8,753,806 B2
(45) Date of Patent: Jun. 17, 2014

(54) ORGAN PROTECTION SOLUTION AND METHOD OF USE

(75) Inventor: Martin Mangino, Powhatan, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/589,441

(22) Filed: Aug. 20, 2012

(65) Prior Publication Data

US 2013/0065217 A1 Mar. 14, 2013

Related U.S. Application Data

(60) Provisional application No. 61/532,153, filed on Sep. 8, 2011.

(51) Int. Cl.
 *A01N 1/00* (2006.01)
(52) U.S. Cl.
 USPC .............................................. 435/1.2; 435/1.1
(58) Field of Classification Search
 None
 See application file for complete search history.

(56) References Cited

U.S. PATENT DOCUMENTS

| | | | | |
|---|---|---|---|---|
| 8,067,150 | B2 * | 11/2011 | Mangino | 435/1.1 |
| 2002/0102720 | A1 * | 8/2002 | Steen | 435/307.1 |
| 2008/0187901 | A1 * | 8/2008 | Doorschodt et al. | 435/1.2 |
| 2009/0298043 | A1 * | 12/2009 | Mangino | 435/1.2 |

* cited by examiner

*Primary Examiner* — Satyendra Singh
(74) *Attorney, Agent, or Firm* — Whitham, Curtis, Christofferson & Cook, PC

(57) ABSTRACT

An organ protectant solution which is intravenously administerable includes a high concentration of cell impermeant molecules which have a charge and/or molecular weight which permit passage across a capillary endothelium and into an interstitial space in said subject but which are too large and/or charged to cross a cell plasma membrane such that said one or more cell impermeant molecules preferentially load into an extracellular fluid compartment can be used to to allow for improved organ harvesting from DCD and brain death donors for transplantation purposes and also can be used extend the "Golden Hour" for traumatic and hemorrhagic shock patients thereby allowing more time for those patients to reach a point of care facility to receive medical treatment.

4 Claims, 2 Drawing Sheets

FIGs 3a-b
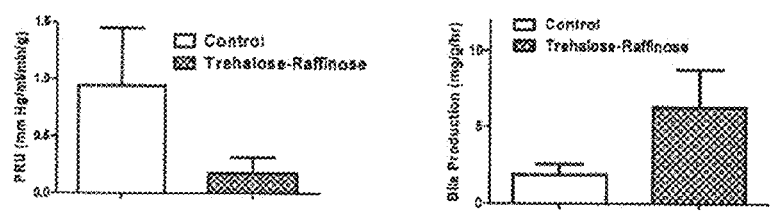
FIG 4.
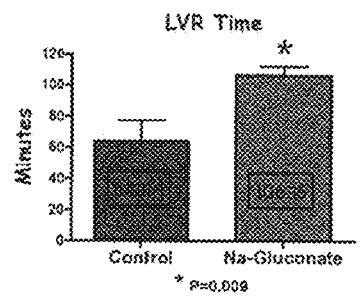
FIG 5.
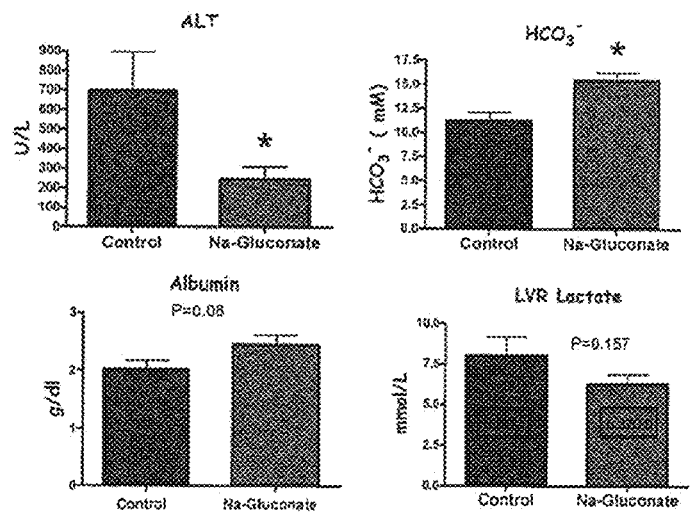

ORGAN PROTECTION SOLUTION AND METHOD OF USE

CROSS-REFERENCE TO RELATED APPLICATIONS

This application claims priority to U.S. Provisional Patent Application No. 61/532,153 filed on Sep. 8, 2011, and the complete contents thereof is herein incorporated by reference.

STATEMENT OF GOVERNMENT INTEREST

This invention was made under a grant from the National Institutes of Health (Grant Number R01 DK087737). The U.S. government may have certain rights under any patent granted hereon.

BACKGROUND

1. Field of the Invention

The invention is directed to organ protectant solutions, and more particularly, to a solution which prevents or reduces in vivo lethal swelling of tissues and organs during periods of warm ischemia due to lack of oxygen delivery and oxygenation.

2. Prior Art

Initial therapy of trauma and hemorrhage shock centers on effective cessation of bleeding and on the infusion of large volumes (2 to 8 liters) to replace lost blood volume. This is considered necessary to restore normal circulatory functions such as arterial blood pressure, cardiac output, oxygen consumption and renal function. Conventionally isotonic fluids are used for high volume resuscitation. Many cellular complications and practical limitations have been cited while using high volume fluids for resuscitation.

Recently, successful resuscitation of hemorrhaged animals and injured patients has been accomplished with low volume hyperosmotic saline solutions. Glucose or mannitol has been tested with less successful results. Small volume resuscitation has been successfully used in some cases using hyperoncotic albumins or high molecular weight tense state polymerized hemoglobin's. The use of hypertonic saline solutions (HS) or colloid solutions (albumin, HES, Hetastarch, Hextend) have had very limited success in clinical trauma and resuscitation, and, due to their mechanism of action, they do not prevent cell swelling.

In the case of uncontrolled donation after cardiac death (DCD) organ donation, controlled DCD organ donation and brain death organ donation, the vital organs are removed from the body as quickly as possible and subsequently the vital organs are preserved in appropriate media to maintain the organ functions. Low volume resuscitation in recently expired patients prior to removal of vital organs to maintain the vitality of the organs and to prevent lethal organ swelling is not usually practiced.

None of these procedures is known to be effective in preventing lethal cell swelling in vivo. In recently expired patients and hemorrhagic shock and trauma patients there is substantial intracellular oxygen deprivation which in turn drops ATP concentration. Due to lack of ATP sodium pump fails, free sodium enters the cell followed by osmotic water movement causing cell swelling. There is no present day technology to deal with cell swelling of organs from DCD donors before harvest or cell swelling in organs in patients with severe shock.

SUMMARY

An embodiment of the invention is an organ protectant solution that protects ischemic organs both for DCD or brain death organ donation for transplantation, and during severe shock and trauma. Prevention of lethal cell swelling in vivo will increase the survivability hemorrhagic shock and trauma patients. Furthermore, if lethal cell swelling can be prevented in vivo before harvest of donating organs, it will substantially increase the percent survival of donating organs and in turn increase the number of organs ready and available for transplantation.

Embodiments of the organ protection solution have been developed on the hypothesis that addition of simple selected cell impermeants (specific anions and small saccharides) in low volume resuscitation solutions, which are easily administered in the field, will prevent lethal cell swelling and improve resuscitation outcome. The organ protection solution protects ischemic organs for donation for transplantation and during severe shock and trauma by preventing tissues from swelling. Cell swelling can produce lethal injury under these conditions and the organ protection solutions described herein target the cell swelling mechanism to make the cells more resistant to damage during flow states.

In use, preferably 150-2000 ml, or more preferably 250-1000 ml, of an organ protectant solution is administered intravenously as quickly as possible after the start of the ischemic event. In the case of DCD organ donor, artificial circulation must by applied.

Of the various small saccharides tested the combination of trehalose-raffinose gave the best results in preventing lethal cell swelling and maintenance of organ vital functions. Other anions and small saccharides may be used as impermeants in the practice of the invention, and organ protectant solutions can include a single impermeant or a mixture of impermeants together with other compounds suitable for the application (e.g., preservatives, anesthetics, etc.). The best impermeants are those with higher molecular weights (e.g., small sacharide or anion with a molecular weight of 342 g/mol or more is preferred). Further, the performance of the organ protectant solution is influenced by the concentration of the impermeants. In general, the organ protectant solutions should have impermeant(s) present at a concentration of 10-60% by weight, and 250-2000 ml (more preferably 250-1000 ml) of organ protectant solution would be required for a 70 kg adult patient (it being recognized that the volume may generally correspondingly be higher or lower depending on the patient size). As discussed in more detail below, the best results were obtained with organ protect solutions including the highest molecular weights at the highest concentration (100 mM or above).

Treating DCD liver donors with impermeants in the pen-death period resulted in significant reduction in vascular resistance to flow and significantly increased bile synthesis at transplantation. This procedure acts as a protectant for organs before harvest from recently expired patients.

DESCRIPTION OF THE DRAWINGS

FIGS. 3a-b are bar graphs illustrating measurements for vascular resistance and bile reduction, respectively, in a DCD model for liver donation;

FIG. 4 is a bar graph illustrating increases in the low volume resuscitation time with cell impermeants in an in vitro model; and FIG. 5 is a collection of bar graphs which show the effect of adding gluconate to LVR solution in liver enzymes, albumin, and metabolic acidosis

DETAILED DESCRIPTION

Figure 1:
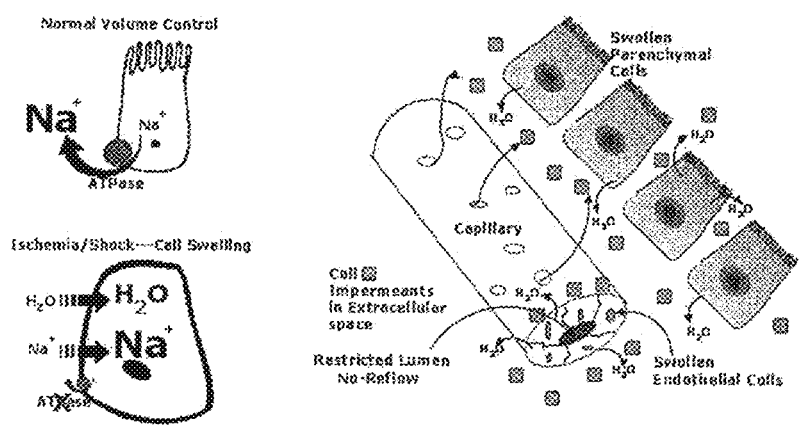
FIG. 1 is a schematic drawing which illustrates the mechanism of action of the organ protectant solutions.

To reduce lethal cell swelling of tissues and organs during periods of warm ischemia due to lack of oxygen delivery and oxygenation, an organ protectant solution containing highly concentrate saccharides and/or anions is provided to the patient as soon as possible. Cell swelling occurs during the harvesting of organs from DCD organ donors and during prolonged periods of shock when medical care is delayed. The organ protect solution may be used before organ donation in recently expired patients. The organ protectant solution may also be given as a protectant for organs to patients in severe hemorrhagic shock and trauma so as to increase the "Golden Hour" before more definitive medical care can be given (e.g., soldiers on a battlefield before evacuation; patients being pulled from traffic accidents, etc.).

The organ protectant solutions of the present invention mitigate lethal cell swelling by preferentially loading the extracellular fluid compartment with molecules that are physically able to escape into the extravascular compartment, but which are impermeable to the cell membrane. This preferentially increases the osmotic force outside of the cell, thereby removing cell water accumulation or preventing water from moving into the cell. These cell impermeant molecules are the active ingredient of the organ protectant solutions of this invention, and they may be present alone or in combination with other suitable constituents (e.g., preservatives, anesthetics, etc.). The molecular weight, size, and charge are specific attributes that allow the molecules to function as cell impermeants. That is, cell impermeants within the practice of the invention have a charge and/or molecular weight which permits them to freely pass across the capillary endothelium and into the interstitial space, but they are too large and/or charged to cross the cell plasma membrane. Thus, they preferentially load into the extracellular fluid compartment where they can exert osmotic effects on both endothelial cells and parenchymal cells.

Examples of cell impermeants with the practice of the invention include specific anions and small saccharides such as sorbitol, gluconate, trehalose, lactobionate, maltitol, raffinose, and combinations thereof. These agents are dissolved in water or a buffer solution (vehicle) such as phosphate buffered saline (PBS), saline, etc., and administered by intravenous infusion (I.V.). They are given in amounts to increase the theoretical extracellular fluid compartment osmolarity of impermeants by 40-100 mM. This may require solutions with impermeants of 10-60% by weight and require 250-1000 ml of solution (for a 70 kg adult patient).

There are some known organ preservation solutions which use molecules such as lactobionic acid or raffinose; however, these solutions are designed to completely flush and replace the extracellular compartment and will not work as an IV solution (and have not been designed to work as an IV solution). This invention differs markedly from these organ preservation solutions in that the invention contemplates a solution formulation and methodology which introduces impermeants into the extracellular space in order to boost the concentrations of the impermeants in the patient to levels that are active for the purposes contemplated herein. The impermeant based organ protect solutions of the present invention are effectively 5× impermeant solutions that when diluted into the patient's extracellular fluid, will raise the impermeant concentration to an effective level to prevent cell swelling. Other organ preservation solutions, which are not used in the manner described herein, may be viewed as essentially a 1× impermeant solution, and they work only when they completely replace the patient's extracellular fluid. That is, if these solutions were used as low volume solution as described herein (something which they were not designed to do and were not previously used in this manner) the final cell impermeant concentration of the patient will be about 20% of an effective concentration and, therefore, will not work. Thus, it should be clear that other preservation solutions that have some agents which may be viewed as a cell impermeant (e.g., lactobionic acid and raffinose) were not designed to dose the extracellular compartment of the patient as contemplated herein, but were designed to replace it with a synthetic solution (i.e., they are best viewed as organ flush out solutions).

The mechanism of action for the organ protectant solutions of the present invention is to prevent lethal cell swelling by the use of cell impermeants. The intracellular concentration of ATP drops in cells when they are deprived of oxygen. Consequent to this is the reduction or arrest of all chemical processes that require intracellular energy (ATP). One of those processes is active cellular volume control. Volume control occurs when the cell actively pumps sodium (Na) out of the cell. This also removes water. When these sodium pumps fail, due to lack of ATP, free sodium enters the cell down an electrochemical gradient, which is followed by electrogenic chloride, and then by osmotic water movement. This causes lethal cell swelling that causes direct cellular injury by cell membrane and mitochondrial injury, and causes further reductions in capillary blood flow and oxygenation (termed the NO REFLOW PHENOMENON) by swelling-induced compression of the microcirculatory exchange vessels (capillaries).

FIG. 1 schematically illustrates the mechanism of action of the organ protectant solutions. The top left of FIG. 1 shows normal volume control in a cell is achieved by pumping sodium out of the cell, while, in contrast, the bottom left of FIG. 1 shows that when the sodium pump stops working due to lack of ATP, the sodium is not pumped out of the cell and the cell enlarges by osmotic water movement into the cell. The right side of FIG. 1 shows that the organ protectant solutions load the extracellular fluid compartment with molecules that are impermeable to the cell membrane. This increases the osmotic forces outside the cell, which in turn either or both removes water from the cells or prevents water from moving into the cell. As shown in FIG. 1, the impermeant molecules have a charge and/or molecular weight that permits them to freely pass across the capillary endothelium and into the interstitial space, but they are too large and/or charged to cross the cell plasma membrane.

The clinical introduction of these impermeants to reduce or prevent lethal cell swelling is via intravenous administration of solutions containing the impermeants. Impermeant organ protectant solutions may be administered immediately after cardiac death in DCD organ donors, which would allow the harvesting and use of livers from these patients that are currently not usable due to severe preservation injury due mainly to lethal cell swelling during the organ donation process. Alternatively, these solutions could be administered to soldiers on a battle field or civilians in the field (e.g., at the scene of an automobile accident) during the low volume state while awaiting more comprehensive medical care. These organ protectant solutions, through preventing lethal cell swelling, buy precious time and allow for traditional organ preservation techniques for the DCD organ or trauma care for the shocked patient.

The organ protectant solutions of this invention (i.e., cell impermeant-based solutions) can be used whenever cell swelling due to warm ischemia is or may be a problem, such as during cardiac arrest periods immediately before donation of organs for transplantation and during hemorrhagic shock and trauma before definitive resuscitation can occur.

In organ preservation, the organ protectant solutions have exemplary uses in:

1. Uncontrolled DCD Organ Donation: These are non-heart beating organ donors that expire in an uncontrolled condition, usually in a hospital emergency room or in the field en-route to an emergency room. The organs are removed much longer after the heart stops due to nature of the patient's death. This typically can be 30 minutes to 2 hours and is the most severe form of preservation injury of organs since it is characterized by the longest warm ischemia times. These organs will most benefit from cell impermeant therapy, provided the impermeant solution can be administered quickly after death is pronounced. These organs typically undergo 30-120 minutes of warm ischemia before they can be surgically removed and flushed with conventional cold preservative solutions. The most susceptible organ under these conditions are the kidney, liver, pancreas, heart and lungs.

2. Controlled DCD Organ Donation: These are non-heart beating organ donors that expire in a controlled condition, usually in a hospital operating room. The organs are removed 10 minutes after the heart stops due to removal from life support. The organs typically undergo 30-60 minutes of warm ischemia before they can be surgically removed and flushed with conventional cold preservative solutions. The most susceptible organ under these conditions are the liver, pancreas, heart and lungs 3. Brain death organ donation of extended criteria donors: These are conventional beating heart, brain dead organ donors, but with complications such as prior periods of warm organ ischemia due to hemodynamic instability or from complications in the donor relating to age, chronic diseases, or pre-existing conditions, which make the organs and tissues more susceptible to ischemic stress-induced cell volume regulation problems.

In hemorrhagic shock and trauma, the organ protectant solutions have exemplary uses in:

1. Combat Casualty Care: The military use for organ protectant solutions may indeed be great. Most injuries and deaths on the battle field are due to severe hemorrhagic shock and trauma secondary to blast injury and high energy projectile impacts. Soldiers must be treated in harsh conditions with low volume resuscitation using simple solutions that are chemically stable in hot conditions. Cell impermeant based low volume resuscitation solutions fit the bill. They have been shown in preliminary studies to extend the time that a subject can remain in the low volume state, which theoretically could extend the "Golden Hour" and allow higher percentages of severely injured soldiers to survive until they reach more definitive trauma care at forward medical hospitals after evacuation from the field. Doubling the "Golden Hour" time is possible and this may have a huge impact on mortality and morbidity.

2. Civilian Trauma Care: Severe hemorrhagic shock and trauma in civilian situations may typically arise from motor vehicle crashes, recreational accidents, and urban violence. Severe hypotension and shock, even when successfully resuscitated, can often lead to secondary hemodynamic problems, infection, and multiple organ failure in the surgical intensive care unit. These patients often die from these secondary complications and there are no good effective treatments. Cell impermeant therapy, given at the time of initial resuscitation, may lower the incidents of these lethal secondary complications or reverse them if they are also administered at the time of their onset, often 12-48 hours after surgery and resuscitation from the initial injury. The target organs for use in shock include the splanchnic organs (liver, intestines, and pancreas) and the lungs. Protecting these organs from lethal cell swelling may be key to mitigating secondary complications and multiple organ failure.

Exemplary Formulation of Cell-impermeant-based Organ Protectant Solution:

Table 1 presents the formulation of one example of a cell-impermeant based organ protectant solution according to the present invention. As discussed herein, the precise formulation of the cell-impermeant based organ protectant solution can vary within the practice of the invention. Specifically, the organ protectant solution should have one or more cell impermeants dissolved or dispersed in a pharmaceutically acceptable vehicle. The cell impermeant(s) will have a charge and/or molecular weight which permits them to freely pass across the capillary endothelium and into the interstitial space of a subject, but they are too large and/or charged to cross the cell plasma membrane such that they preferentially load into the extracellular fluid compartment where they can exert osmotic effects on both endothelial cells and parenchymal cells. They are given in amounts to increase the theoretical extracellular fluid compartment osmolarity of impermeants by 40-100 mM. This may require solutions with impermeants of 10-60% by weight and require 250-1000 ml of solution (for a 70 kg adult patient).

TABLE 1

| Cell Impermeants | Concentrations | g/L (1.5M) |
|---|---|---|
| Sorbitol | 0-1.5M | 273 |
| Gluconate (Na) | 0-1.5M | 294 |
| Trehalose | 0-1.5M | 513 |
| Raffinose | 0-1.5M | 891 |
| Lactobionate (Na) | 0-1.5M | 597 |
| Maltitol | 0-1.5M | 516 |
| Combinations | 1.5M Total | — |

1 liter is recommended per patient (75 kg) to achieve the desired effect. The vehicle is phosphate buffered saline (PBS).

Exemplary Method of Administration of the Cell Impermeant-based Organ Protectant Solutions:

The general rule of thumb should be to start administration of the organ protection solutions as quickly as possible after the start of the ischemic event (e.g., cardiac death in organ donation or cardiovascular collapse in shock). Give the solutions through an intravenous catheter like any I.V. fluid. If the patient is a DCD organ donor, artificial circulation should be applied for a few minutes with external or internal cardiac message or an autopulse vest in order to circulate the impermeants. For administration during shock, these solutions can be part of the resuscitation fluids. The solutions can be stored in convenient Viaflex bags for storage, transportation, and use. Typical administered volumes may be 500-2000 ml per patient or they also maybe given by constant infusion in the intensive care unit (ICU) during recovery from surgery and resuscitation.

The examples below demonstrate the use of cell impermeants in organ protectant solutions for both donation of DCD organs and in hemorrhagic shock, and show that the organ protectant solutions prevent or reduce lethal cell swelling.

EXAMPLES

Example 1

Organ Donation and Preservation from DCD Donors: A series of experiments were performed to explore the optimal impermeant effect of a family of likely useful impermeants. The variables chosen were
The molecular species of impermeant
The best concentration (in the extracellular space)
The best time of administration For these experiments, the impermeants used included specific anions and small saccharides such as sorbitol, gluconate, trehalose, lactobionate, maltitol, raffinose, and combinations of the same. These agents were dissolved in water of buffer solution such phosphate buffered saline and administered by intravenous infusion.

Figure 2:
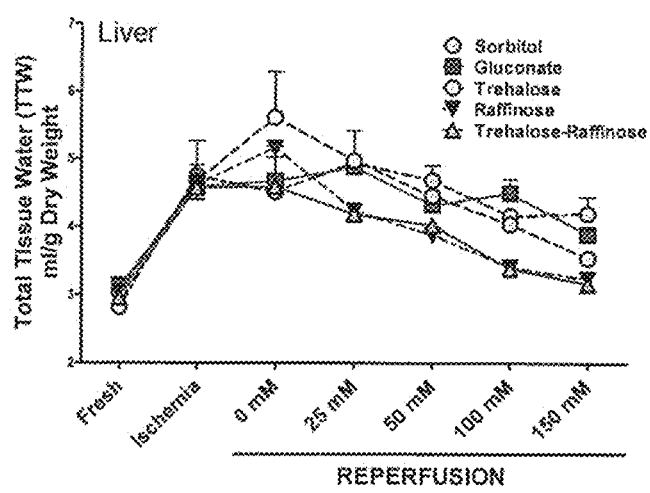
FIG. 2 is a graph showing the effects impermeants have on swelling of liver slices.

FIG. 2 illustrates the effect of various impermeants on cell swelling of liver slices. The outcome variable was cell swelling of liver tissue slices exposed to periods of warm ischemia and reperfusion to mimic the conditions that a DCD donor liver would encounter. For these experiments, the best impermeant solution had the highest molecular weight and highest concentration (e.g., trehalose has a molecular weight of 342 g/mol, and best results were obtained with concentrations of 100 mM or above). However, combinations of high and moderate molecular weight impermeants also proved to work well.

In this model, liver tissue weight almost doubled after ischemia due to cell swelling from water accumulation. Cell impermeants in the extracellular space largely prevented or attenuated this increase. From these in vitro data, an optimized impermeant for in vivo use in DCD liver donation may include mixtures of trehalose and raffinose at about 50 mM each, and the organ protectant solution should be given at the time of ischemia (cardiac death) in order to mitigate lethal cell swelling of the liver tissue, and presumably, to lessen preservation injury and enhance post-transplant performance. This will significantly increase organ availability, reduce wait list times, and save lives.

FIGS. 3a-b show the effect of cell-impermeant based organ protection solutions on a DCD model for liver donation. Adult donor rats were anesthetized and a bilateral pneumothorax was induced, which caused heart failure in 2 minutes. Then, 30 minutes of time was allowed to elapse to simulate warm ischemia in the DCD patients. At the time of heart failure, animals were assigned to either a control group that received about 3 ml of PBS vehicle I.V. over 10 minutes or an experimental group that was given about 3 ml of a trehalose and raffinose solution in PBS (about 750 mM each), I.V. over 10 minutes. Each animal also was given heparin and phentolamine at the time of cardiac death. After 30 min of in-situ warm ischemia, the liver was harvested and flushed with UW solution and cold stored for 24 hours. The livers were reperfused on an isolated perfused liver preparation (IPL) in-vitro for 60 minutes to assess post-reperfusion liver function (preservation injury). FIGS. 3a and 3b respectively show vascular resistance and bile production for both groups.

FIGS. 3a-b show that treating DCD liver donors with impermeants in the peri-death period resulted in significant reductions in vascular resistance to flow and significantly increased bile synthesis at reperfusion (transplantation). These results clearly indicate less preservation injury with the use of cell impermeants in DCD donors that may prevent lethal delayed graft function in livers harvested from these patients. This may provide enough functional protection to allow for their use in human liver transplantation and greatly expand the donor pool.

Example 2

Hemorrhagic shock model in rodents: Gluconate was administered in the organ protectant solution (e.g., a low volume resuscitation (LVR) solution with cell impermeants according to the present invention) in order to achieve a theoretical gluconate concentration of about 60 mM in the extracellular fluid compartment (subsequent experiments have shown that about 100 mM is probably optimal). The idea of low volume resuscitation is to give the shocked patient small volumes of intravenous fluids to prolong the time on the field to allow for rescue and transport to a forward hospital where more definitive resuscitation can occur (due to fewer resource limitations). The purpose of the addition of the cell impermeants to the LVR solution (usually saline) was to increase this "down time" further, effectively increasing the tolerance to the low flow state and making it more likely that the patient can survive the wait to the hospital. Essentially, the objective is to increase the "Golden Hour".

FIG. 4 shows measurements of the LVR time period, a measure of the "Golden Hour". In our shock experiments, the time that the control animals could remain in the low volume state (after LVR administration) was 64 minutes. However, when gluconate was added to the LVR solution, significantly enhanced the LVR time to over 106 minutes. This means that these subjects were able to stay safely in the low volume state for much longer periods. This means that they can wait longer for transport and full resuscitation and presumably have a higher chance of survival.

In support of the finding with respect to FIG. 4 is the finding that gluconate treated subjects also had less liver injury and better metabolism 24 hours after shock and resuscitation. Specifically, FIG. 5 illustrates the effect of adding gluconate to LVR solution in liver enzymes, albumin, and metabolic acidosis. Liver enzymes were lower and albumin was higher in the gluconate group. Likewise, there was less metabolic acidosis in the gluconate group. Furthermore, the subjects in the gluconate group were kept in the low volume state much longer than the controls. So, they suffered much more hypotension (because the gluconate increased the low volume time) but they still did better the next day, compared to the controls.

The invention claimed is:

1. A method for organ preservation in donation after cardiac death (DCD) or brain death donors, comprising the steps of:
after cardiac or brain death in a subject is pronounced, administering intravenously to said subject a sufficient quantity of an organ protection solution which has one or more cell impermeant molecules selected from the group consisting of sorbitol, gluconate, trehalose, raffinose, lactobionate, and maltitol, and at least one of said one or more cell impermeant molecules is present at a concentration of at least 60 mM, which are pharmaceutically acceptable and can cross a capillary endothelium and into an interstitial space in said subject, wherein said one or more cell impermeant molecules preferentially load into extracellular fluid in an extracellular fluid compartment of said subject and increase a theoretical extracellular fluid osmolarity of said subject by 40-100 mM without entering one or more of endothelial and parenchymal cells within a treatment period of 30 to 120 minutes; and preventing or reducing cell swelling of organs of said subject using said one or more cell impermeant molecules to exert osmotic effects on one or more of endothelial cells and parenchymal cells, wherein prevention or reduction of cell swelling continues until harvesting of one or more organs from said subject.

2. The method of claim 1, further comprising the step of applying artificial circulation to said subject.

3. The method of claim 1, wherein said organ protectant solution includes both trehalose and raffinose.

4. The method of claim 1, wherein at least one of said one or more cell impermeant molecules is present at a concentration of at least 100 mM.

\* \* \* \* \*